(12) United States Patent
Vamvakas et al.

(10) Patent No.: US 9,504,656 B2
(45) Date of Patent: Nov. 29, 2016

(54) PHARMACEUTICAL COMPOSITIONS FOR POORLY SOLUBLE ACTIVE INGREDIENTS

(71) Applicant: Banner Life Sciences, LLC, High Point, NC (US)

(72) Inventors: George Vamvakas, Greensboro, NC (US); Aqeel A. Fatmi, High Point, NC (US)

(73) Assignee: Banner Life Sciences, LLC, High Point, NC (US)

( * ) Notice: Subject to any disclaimer, the term of this patent is extended or adjusted under 35 U.S.C. 154(b) by 26 days.

(21) Appl. No.: 14/518,188

(22) Filed: Oct. 20, 2014

(65) Prior Publication Data

US 2015/0108033 A1    Apr. 23, 2015

Related U.S. Application Data

(60) Provisional application No. 61/893,721, filed on Oct. 21, 2013.

(51) Int. Cl.
*A61K 9/48* (2006.01)
*A61K 31/445* (2006.01)
*A61J 3/07* (2006.01)

(52) U.S. Cl.
CPC ........... *A61K 9/4866* (2013.01); *A61K 9/4858* (2013.01); *A61K 31/445* (2013.01); *A61J 3/07* (2013.01)

(58) Field of Classification Search
None
See application file for complete search history.

(56) References Cited

U.S. PATENT DOCUMENTS

| | | | |
|---|---|---|---|
| 5,146,730 A | 9/1992 | Sadek et al. | |
| 5,459,983 A | 10/1995 | Sadek et al. | |
| 6,482,516 B1 | 11/2002 | Sadek et al. | |
| 7,910,553 B2 | 3/2011 | Mitra et al. | |
| 2006/0115527 A1* | 6/2006 | Hassan | A61K 9/4875 424/457 |
| 2006/0165778 A1 | 7/2006 | Hassan et al. | |
| 2007/0027213 A1* | 2/2007 | Oberegger | A61K 9/2027 514/563 |
| 2007/0142266 A1 | 6/2007 | Loscher et al. | |
| 2010/0087492 A1* | 4/2010 | Johnson | A61K 31/44 514/341 |
| 2014/0073670 A1* | 3/2014 | Badabhagni | A61K 31/4545 514/315 |

* cited by examiner

*Primary Examiner* — Robert A Wax
*Assistant Examiner* — Quanglong Truong
(74) *Attorney, Agent, or Firm* — Brinks Gilson & Lione

(57) ABSTRACT

Described herein are pharmaceutical compositions for the delivery of poorly soluble active pharmaceutical ingredients. In particular, a substantially clear fexofenadine HCl solution in a soft gelatin capsule is described.

20 Claims, 3 Drawing Sheets

PHARMACEUTICAL COMPOSITIONS FOR POORLY SOLUBLE ACTIVE INGREDIENTS

CROSS REFERENCE TO RELATED APPLICATIONS

This application claims priority to U.S. Provisional Patent Application No. 61/893,721, filed Oct. 21, 2013, which is incorporated by reference herein in its entirety.

TECHNICAL FIELD

Described herein are pharmaceutical compositions for the delivery of poorly soluble active pharmaceutical ingredients. In particular, a substantially clear fexofenadine HCl solution in a soft gelatin capsule is described.

BACKGROUND

Solubilizing hydrophobic and amphiphilic active drug substances for efficient oral delivery remains a problem. At the minimum, an efficient drug delivery system should function to deliver a therapeutically effective dosage of any given compound to achieve the desired therapeutic concentration. Maximum strength formulations provide higher doses of active drug substances and therapeutic efficacy while minimizing the number of doses required. These formulations can increase patient satisfaction and compliance; however, they can be challenging to formulate for poorly soluble active drug substances often because of precipitation of the active, and often these drugs are formulated as tablets or as a suspension.

Soft capsules have gained popularity and acceptance over tablets and hard capsules due to their elegant and clear appearance. Soft capsules are in general easier to swallow, are hermetically sealed, and can easily be colored to protect ingredients from light. Additionally, soft capsules often allow for increased absorption and bioavailability by the large range of methods for preparing active drug ingredients and matrix fills.

Current methodologies for increasing the solubility of poorly soluble active drug substances for use in soft capsules include the development of emulsion type matrices of either oil in hydrophilic (o/p) or hydrophilic in oil (p/o). These can include both microemulsions (about 10-200 nm) and macroemulsions (>1000 nm). Such emulsions are typically generated by the solubilization of the active ingredient in an oil phase, which is then dispersed in an aqueous environment with a surfactant. These formulations can often become visibly cloudy or discolored to the naked eye. Furthermore, typically used emulsions can be thermodynamically unstable leading to phase separation and reduced bio absorption. Even microemulsion systems, such as self-microemulsifying drug delivery systems (SMEDDS), which are inherently more stable than standard emulsions can become unstable depending on changes in temperature and pH. Moreover, microemulsions require large amounts of surfactant to stabilize the microemulsion, which may exceed safe levels for ingestion.

In addition, many hydrophobic and amphiphilic drugs are exported by the P-glycoprotein (P-gp) efflux active transporter leading to decreased in vivo permeability. For example, this process of active efflux leads to multi-drug resistance mechanisms in cancer and decreased absorption and bioavailability of many anti-cancer drugs. In addition, many other hydrophobic and amphiphilic drugs are highly susceptible to P-gp mediated efflux due to interactions with the cellular bilayer lipid membrane. In particular, substrates of the P-gp transporter are most commonly amphiphilic, and thus, have spatially separate hydrophilic and hydrophobic moieties. One approach described in US Patent Application Publication No. US 20070142266 is to couple a drug that is a P-gp substrate with a P-gp inhibitor to minimize P-gp-mediated export. While there are numerous direct and indirect P-gp inhibitors available, each of these inhibitors can have unintended side effects and may not be compatible with all active drug ingredients. Other approaches are in modifying the salt form of the active drug ingredient to lower the affinity between the P-gp efflux transporter and drug. Another approach described in U.S. Pat. No. 7,910,553 includes generating prodrug forms of an active ingredient with P-gp protective amino acid sequences. These approaches, however, can decrease the bio absorption of a drug and change its pharmacokinetics. Thus, the ideal P-gp inhibitor should have no pharmacological activity and be non-toxic.

Accordingly, there is an unmet need in the field for soft capsule pharmaceutical formulations that are suitable for poorly soluble active drug substances, which increase bioavailability and inhibit or reduce the affinity of the P-gp transporter for poorly soluble active drug substances.

SUMMARY

Described herein are pharmaceutical formulations suitable for poorly soluble active drug substances that in some embodiments may inhibit or reduce the affinity of the P-gp transporter for the poorly active drug substances described herein. In some aspects, the pharmaceutical formulations described herein may further increase the permeability of the active drug substances described herein.

One embodiment described herein is an oral pharmaceutical composition comprising a matrix fill comprising at least one solubility enhancing agent, at least one viscosity enhancing agent, at least one surfactant, at least one pH modifying agent, water, and at least one active pharmaceutical ingredient; wherein the matrix fill is encapsulated in a soft capsule shell. In one aspect, the solubility enhancing agent comprises about 40% to about 85% of the matrix fill mass. In another aspect, the viscosity enhancing agent comprises from about 1% to about 10% of the matrix fill mass. In another aspect, the surfactant comprises from about 1% to about 7% of the matrix fill mass. In another aspect, water comprises about 1% to about 7% of the matrix fill mass. In another aspect, the pH-modifying agent comprises about 1% to about 3% of the matrix fill mass. In another aspect, the active pharmaceutical ingredient comprises about 5% to about 33% of the matrix fill mass. In another aspect, the ratio of the active pharmaceutical ingredient to the total mass of the matrix fill is about 1:20 to about 1:3.

In one aspect, the solubility enhancing agent comprises polyethylene glycol, propylene glycol, or glycerol. In another aspect, the solubility enhancing agent comprises polyethylene glycol and propylene glycol. In another aspect, polyethylene glycol has a molecular weight of about 200 to about 1000.

In one aspect, the viscosity enhancing agent comprises povidone, hydroxypropylmethylcellulose, hydroxypropylcellulose, gelatin, methylcellulose, acacia, xanthan gum, or tragacanth.

In one aspect, the surfactant comprises an anionic surfactant. In another aspect, the anionic surfactant comprises sodium lauryl sulfate, sodium docusate, sodium stearate, or ammonium lauryl sulfate.

In one aspect the pH-modifying agent comprises a carboxylic acid. In another aspect, the pH-modifying agent comprises tartaric acid, lactic acid, glutamic acid, aspartic acid, malic acid, succinic acid, or fumaric acid.

In one aspect, the matrix fill comprises an active pharmaceutical ingredient that is poorly soluble in water. In another aspect, the poorly soluble active pharmaceutical ingredient comprises: acetaminophen, acetazolamide, acyclovir, allopurinol, amoxicillin, cefdinir, cefixime, cefotiam hexetil hydrochloride, cefpodoxime proxetil, cefuroxime axetil, dapsone, dexamethasone, doxycycline, famotidine, fexofenadine, folic acid, furosemide, glipizide, griseofulvin, hydrochlorothiazide, l-carbocysteine, levodopa, levosulpiride, linezolid, meloxicam, mesalamine, metoclopramide, modafinil, nabumetone, nalidixic acid, oxcarbazepine, oxycodone, phenobarbital, propylthiouracil, sulfadiazine, sulfamethoxazole, sultamicillin, theophylline, tosufloxacin, triflusal, trimethoprim, and zaltoprofen or pharmaceutically acceptable salts, isomers, prodrugs (e.g., esters) and derivatives thereof, and mixtures of any of the active pharmaceutical ingredients listed thereof. In another aspect, the active pharmaceutical ingredient comprises fexofenadine. In another aspect, fexofenadine comprises about 5% to about 33% of the total matrix fill mass.

In one aspect, the matrix fill comprises polyethylene glycol, propylene glycol, povidone, sodium lauryl sulfate, citric acid, water, and fexofenadine. In another aspect, the matrix fill comprises: about 45% to about 65% polyethylene glycol 400; about 10% to about 20% propylene glycol; about 1% to about 5 povidone K90; about 2% to about 6% sodium lauryl sulfate; about 1% to about 3% citric acid; about 1% to about 3% water; and about 5% to about 20% fexofenadine hydrochloride. In another aspect, the matrix fill is clear or transparent. In another aspect, the matrix fill is stable for at least about 6 months at 25° C. and 60% relative humidity.

One embodiment described herein is a matrix fill suitable for encapsulation in a soft capsule shell comprising about 59% polyethylene glycol 400, about 15% propylene glycol, about 3.3% povidone K90, about 4.2% sodium lauryl sulfate, about 1% citric acid, about 2.5% water, and about 15% fexofenadine hydrochloride.

In one aspect, the soft capsule shell comprises a film forming polymer, a plasticizer, a solvent, a pH modifying agent; and optionally, an opacifying agent, a coloring agent, or a pharmaceutical excipient. In another aspect, the film forming polymer comprises gelatin, the plasticizer comprises glycerol, the pH modifying agent comprises citric acid, and the opacifying agent comprises titanium oxide. In another aspect, the soft capsule shell comprises about 43% of at least one film-forming polymer, about 20% of at least one plasticizer, about 36% of a solvent, about 1% of a pH modifying agent; optionally, about 0.7% of an opacifying agent; and optionally, about 0.1% of at least one coloring agent.

One embodiment described herein is an oral pharmaceutical composition comprising a soft capsule shell and matrix fill, wherein the matrix fill comprises about 45% to about 65% polyethylene glycol 400, about 10% to about 20% propylene glycol, about 1% to about 5 povidone K90, about 2% to about 6% sodium lauryl sulfate, about 1% to about 3% citric acid, about 1% to about 3% water, and about 5% to about 20% fexofenadine hydrochloride; wherein the soft capsule shell comprises about 43% gelatin, about 19% glycerol, about 37% water, about 1% citric acid, and about 0.7% titanium oxide.

One embodiment described herein is a method for manufacturing a matrix fill composition comprising at least one solubility enhancing agent, at least one viscosity enhancing agent, at least one surfactant, at least one pH modifying agent, water, and at least one active pharmaceutical ingredient suitable for encapsulation in a soft capsule shell; wherein preparing the matrix fill comprises the steps of: (a) wetting and mixing the surfactant in water; (b) adding the one or more solubility enhancing agents and the one or more pH modifying agents and stirring the mixture; (c) adding the active pharmaceutical ingredient and stirring the mixture; (d) adding the viscosity enhancing agent and stirring the mixture; (e) filtering the mixture through a filter cloth; and (f) degassing the matrix fill mixture. In one aspect, the matrix fill composition in the matrix fill manufacturing method described herein comprises polyethylene glycol, propylene glycol, povidone, sodium lauryl sulfate, citric acid, water, and fexofenadine. In another aspect, the matrix fill composition in the matrix fill manufacturing method described herein comprises: about 45% to about 65% polyethylene glycol 400, about 10% to about 20% propylene glycol, about 1% to about 5 povidone K90, about 2% to about 6% sodium lauryl sulfate, about 1% to about 3% citric acid, about 1% to about 3% water, and about 5% to about 20% fexofenadine hydrochloride. In another aspect, the matrix fill prepared by the matrix fill manufacturing method described herein is clear or transparent. In another aspect, the matrix fill prepared by the matrix fill manufacturing method described herein is stable for at least about 6 months at 25° C. and 60% relative humidity. In another aspect, the matrix fill prepared by the matrix fill manufacturing method described herein has a pH of about pH 3.5 to about pH 7.5.

One embodiment described herein is a method for manufacturing an oral pharmaceutical composition comprising a soft capsule shell and matrix fill comprising the steps of: (a) providing a matrix fill as described herein prepared by the methods of manufacturing matrix fills described herein, (b) providing a soft capsule gel mass or an enteric soft capsule gel mass, (c) casting the soft capsule gel mass into films using heat-controlled drums or surfaces, and (d) forming a soft capsule comprising the matrix fill composition using rotary die encapsulation technology.

One embodiment described herein is a soft capsule comprising a matrix fill described herein produced by the method of manufacturing matrix fills described herein. Another embodiment described herein is an enteric soft capsule comprising a matrix fill described herein produced by the method of manufacturing matrix fills described herein One embodiment described herein is a method for treating, reducing the symptoms or onset of, or prophylaxis of stemming from seasonal allergic rhinitis or chronic idiopathic urticaria with the oral pharmaceutical compositions described herein. In one aspect, the oral pharmaceutical compositions described herein comprises an anti-allergenic. In another aspect, the anti-allergenic comprises fexofenadine.

One embodiment described herein is a kit for dispensing the oral pharmaceutical compositions described herein comprising: at least one soft capsule comprising a matrix fill comprising an active pharmaceutical ingredient; at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally, an insert comprising instructions or prescribing information for the active pharmaceutical ingredient.

DETAILED DESCRIPTION

Figure 1:
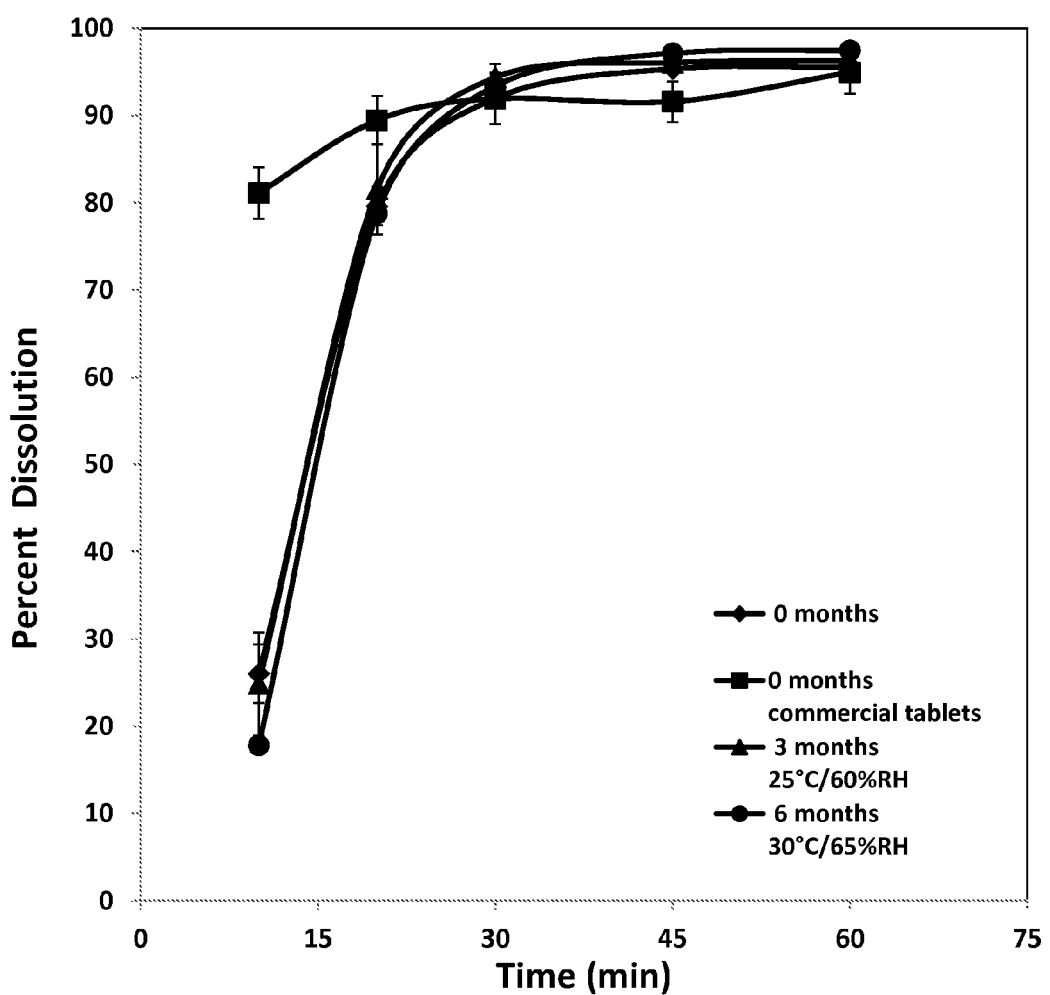
FIG. 1. Dissolution kinetics of soft gelatin capsules with 180 mg fexofenadine HCl matrix fills after different storage times.

The term "active ingredient" or "active pharmaceutical ingredient" "active pharmaceutical agent" or active drug substance as used herein refers to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The term "formulation" or "composition" as used herein refers to the active pharmaceutical ingredient or drug in combination with pharmaceutically acceptable excipients. This includes orally administrable formulations as well as formulations administrable by other means.

The term absolute bioavailability as used herein refers to the fraction of a drug or active pharmaceutical ingredient absorbed through non-intravenous administration (e.g., oral administration) to intravenous administration of the same drug or active pharmaceutical ingredient.

The term "permeability" as used herein refers to the extent of absorption (or fraction of dose absorbed) of an active drug substance across a biological membrane. The permeability (e.g., low permeability or high permeability) of an active drug substance can be determined by pharmacokinetic studies in mammals, e.g., mass balance studies, absolute bioavailability studies, or intestinal permeability methods known in the art. In one aspect, an active drug substance can be classified as being highly permeable if the extent of in vivo absorption is greater than 90% as determined by mass-balance studies or comparison to an intravenous dose. In another aspect, an active drug substance can be classified as having low permeability if the extent of absorption is less than about 90%, about 80%, about 70%, about 60%, about 50%, about 40%, about 30%, about 20%, 10%, or the active drug substance has no measurable absorption (i.e., 0%). See, *FDA Guidance for Industry: Waiver of In Vivo Bioavailability and Bioequivalence Studies for Immediate-Release Solid Oral Dosage Forms Based on a Biopharmaceutics Classification System*, August 2000, which is incorporated by reference herein for such teachings.

The phrase "poorly soluble" or "poorly soluble active ingredient" or "poorly soluble active pharmaceutical ingredient" as used herein refers to an active pharmaceutical agent or drug in an amount equal to its maximum dose strength that is not fully soluble in about 250 mL or less of an aqueous media across a pH range of about 1 to about 7.5. The term "poorly soluble" as used herein also encompasses all active pharmaceutical ingredients designated as having a "low solubility" by the BCS Classification system. In some aspects, the maximum dose of depends on the active pharmaceutical ingredient and may be from about 1 mg to about 2000 mg, including all iterations of integers within the specified range. See, *FDA Guidance for Industry: Waiver of In Vivo Bioavailability and Bioequivalence Studies for Immediate-Release Solid Oral Dosage Forms Based on a Biopharmaceutics Classification System*, August 2000, which is incorporated by reference herein for such teachings.

The phrase "minimal solubility in water" encompasses compounds that are either sparingly soluble (i.e., 30-100 parts of solvent per solute), slightly soluble (i.e., 100-1000 parts of solvent per solute), very slightly soluble (i.e., 1,000-10,000 parts of solvent per solute) or practically insoluble or insoluble in water (i.e., >10,000 parts of solvent per solute).

The term "BCS Class I, II, II, or IV" refers to whether a compound or active drug substance has high or low permeability and high or low solubility (e.g., poorly soluble). BCS Class I drugs have high permeability and high solubility; BCS Class II drugs have high permeability and low solubility, BCS Class III drugs have low permeability and high solubility, and BCS Class IV drugs have low permeability and low solubility. See, *FDA Guidance for Industry: Waiver of In Vivo Bioavailability and Bioequivalence Studies for Immediate-Release Solid Oral Dosage Forms Based on a Biopharmaceutics Classification System*, August 2000, which is incorporated by reference herein for such teachings.

The term room temperature as used herein refers to common ambient temperatures found in pharmaceutical laboratories ranging from about 20° C. to about 27° C.

The term "controlled release" as used herein refers to a composition that does not immediately releases an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "modified release" as used herein refers to a composition that releases an active ingredient at a slower rate than does an immediate release formulation under physiological conditions or in an in vitro test.

The term "sustained" release" as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of at least 18 hours under physiological conditions or in an in vitro assay.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any value that is within a variation of up to ±10% of the value modified by the term "about."

As used herein, "a" or "an" means one or more unless otherwise specified.

Terms such as "include," "including," "contain," "containing" and the like mean "comprising."

The term "or" can be conjunctive or disjunctive.

In one embodiment, the matrix fill comprises a surfactant. The surfactant can be cationic, anionic, non-ionic, or zwitterionic. The surfactant can have a hydrophilic/lipophilic balance (HLB) value between about 1 and about 20 and a melting point between about 25° C. and about 70° C. The HLB characteristic of surfactants are known in the art. See *Physical Pharmacy: Physical Chemical Principles in the Pharmaceutical Sciences*, Lippincott Williams & Wilkins, Philadelphia, Pa., 4th Edition, pp. 371-373, 1993, which is incorporated by reference herein for such teachings.

Suitable non-limiting examples of non-ionic surfactants include: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F. 127 NF, Pluronic® F. 127 NF 500 BHT Prill, Pluronic® F. 127 NF Prill, Poloxamer 407, Pluronic® F 38, Pluronic® F 38 Pastille, Pluronic® F 68, Pluronic® F 68 LF Pastille, Pluronic® F. 68 NF, Pluronic® F. 68 NF Prill, Poloxamer 188, Pluronic® F. 68 Pastille, Pluronic® F. 77, Pluronic® F. 77 Micropastille, Pluronic® F. 87, Pluronic® F. 87 NF, Pluronic® F. 87 NF Prill, Poloxamer 237, Pluronic® F. 88, Pluronic® F. 88 Pastille, Pluronic® F. 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen 464, Alkanol 6112, Brij® 52, Brij® 93, Brij® S2, Brij® S, Brij® 58, Brij® C10, Brij® L4, Brij® O10, Brij® O10, BRIJ® 020, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl FS-300, or Zonyl FSN.

Suitable anionic surfactants include for example, salts of perfluoro carboxylic acids and perfluoro sulphonic acid, alkyl sulphate salts such as sodium lauryl sulfate (sodium dodecyl sulphate) and ammonium lauryl sulphate, sulphate ethers such as sodium lauryl ether sulphate, and alkyl benzene sulphonate salts; sulfonate containing surfactants such as sodium docusate (dioctyl sodium sulfosuccinate (DSS)), calcium docusate, and potassium docusate; sodium alkyl sulfoacetates, such as sodium lauryl sulfoacetate. Non-limiting examples include aluminum monostearate, ammonium lauryl sulfate, calcium stearate, dioctyl calcium sulfosuccinate, dioctyl potassium sulfosuccinate, dioctyl sodium sulfosuccinate, emulsifying wax, magnesium lauryl sulfate, magnesium stearate, mono-, di-, or triethanolamine lauryl sulfate, potassium oleate, sodium castor oil, sodium cetostearyl sulfate, sodium lauryl ether sulfate, sodium lauryl sulfate, sodium lauryl sulfoacetate, sodium oleate, sodium stearate, sodium stearyl fumarate, sodium tetradecyl sulfate, zinc oleate, zinc stearate. Suitable cationic surfactants include, but are not limited to, for example, quaternary ammonium compounds such as benzalkonium chloride, cetylpyridinium chlorides, benzethonium chlorides, and cetyl trimethylammonium bromides or other trimethylalkylammonium salts.

Zwitterionic surfactants include for example, but are not limited to dodecyl betaines, coco amphoglycinates and cocamidopropyl betaines.

In another embodiment described herein, the matrix fill includes a pH modifying agent that is an acid. Suitable organic acids are those containing one or more acidic groups, e.g., acidic groups comprising carboxylic and sulfonic acid groups. Suitable water-soluble organic acids include water-soluble organic acids selected from mono-, di- or polybasic carboxylic acids or mono-, di or tri-sulfonic acids, e.g., which are solid at ambient temperature. Suitable solid water-soluble carboxylic acids include aliphatic mono or poly-carboxylic acids, e.g., containing from 2 to 8 carbon atoms, particularly from 2 to 6 carbon atoms, e.g., all- or tricarboxylic acids containing from 4 to 6, e.g., 4 carbon atoms, e.g., saturated or unsaturated. Examples of suitable solid water-soluble aliphatic mono-carboxylic acids include sorbic acid (2,4-hexadienoic acid). Examples of suitable solid water-soluble aliphatic di-carboxylic acids include adipic, malonic, succinic, glutaric, maleic or fumaric acid. The aliphatic carboxylic acid may be optionally substituted by one or more groups, e.g., 1, 2 or 3 groups, which may be the same or different, selected from carboxy, amino, and hydroxy. Suitable substituted solid water-soluble aliphatic carboxylic acids include, for example, hydroxy substituted aliphatic mono-carboxylic acids such as gluconic acid, solid forms of lactic acid, glycolic acid or ascorbic acid; hydroxy substituted aliphatic di-carboxylic acids such as malic, tartaric, tartronic (hydroxymalonic), or mucic (galactaric) acid; hydroxy −2s substituted aliphatic tri-carboxylic acids, for example, citric acid; or amino acids carrying an acidic side chain, such as glutamic acid or aspartic acid. Suitable aromatic carboxylic acids include water-soluble aryl carboxylic acids containing up to 14 carbon atoms. Suitable aryl carboxylic acids comprise an aryl group, for example, a phenyl or naphthyl group which carries one or more carboxyl groups, e.g., 1, 2, or 3 carboxy groups. The aryl group is optionally substituted by one or more groups, e.g., 1, 2, or 3 groups, which may be the same or different, selected from hydroxy, (1-4C) alkoxy, e.g., methoxy and sulfonyl. Suitable aryl carboxylic acids include benzoic, phthalic, isophthalic, terephthalic or trimellitic acid (1,2,4-benzenetricarboxylic acid).

In one embodiment, the pH modifying agent decreases the pH of the encapsulated matrix fill compositions described herein and reduces or inhibits the precipitation of the active pharmaceutical ingredients described herein. In one aspect, the pH modifying agent reduces or inhibits crosslinking of the active pharmaceutical ingredients described herein with the soft capsule shells described herein.

In one embodiment, the matrix fill described herein has a pH of about pH 3.5 to about pH 8.5. In another embodiment, the matrix fill described herein has a pH of about pH 3.5 to about pH 7.5. In one aspect, the matrix fill described herein has a pH of about 7.5. In one aspect, the matrix fill described herein has a pH of about 6.5. In one aspect, the matrix fill described herein has a pH of about 5.5. In one aspect, the matrix fill described herein has a pH of about 4.5. In one aspect, the matrix fill described herein has a pH of about 3.5.

In another embodiment, it is preferred for the matrix fill to have a pH of less than about 5.5. Without being bound by any theory, it is thought that the soft capsule shells described herein can shift the pH of the matrix fill described herein to be more alkaline. Therefore, in one aspect, a pH of less than 5.5 prevents or reduces the precipitation of the active pharmaceutical ingredients described herein.

In another embodiment, the matrix fill comprises at least one solubility enhancing agent. Useful solubility enhancing agents for the matrix fills described herein include Capmul® MCM, Captex® 355, Cremophor® RH 40, Croscarmellose, Crospovidone, Crospovidone CL, Crospovidone CL-F, Crospovidone CL-M, glycerol, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 200, polyethylene glycol 400, polyethylene glycol 600, polyethylene glycol 800, polyethylene glycol 1000, polyethylene glycol 2000, polyethylene glycol 3350, Plurol®, propylene glycol, and Oleique CC 497.

In another embodiment, the matrix fill comprises a viscosity enhancer that increases the viscosity of the matrix fill. In one embodiment, the viscosity enhancer includes polyvinylpyrrolidone (e.g., Povidone K 12, Povidone K 17, Povidone K 30, Povidone K 90), copovidone, hydroxypropylmethylcellulose, hydroxypropylcellulose, ethyl cellulose, methylcellulose, and polyethylene oxide. Additional suitable viscosity enhancers include a modified cellulose, a modified polysaccharide, a non-ionic gum, acacia, acacia, agar, alginic acid, aluminum monostearate, bentonite, carbomer, carbomers such as Carbopol® 934, Carbopol® 940, Carbopol® 941, Carbopol® 974P, Carbopol® copolymers, carboxymethylcellulose, carboxymethylcellulose calcium, carboxymethylcellulose sodium, carboxymethylcellulose sodium 12, carrageenan, colloidal silicon dioxide, copolymer of polyvinylpyrrolidone and polyvinyl acetate, dextrin, gelatin, gellan gums, Gelucire® 33/01, Gelucire® 37/02, Gelucire® 39/01, Gelucire® 43/01, Gelucire® 44/14, Gelucire® 50/02, Gelucire® 50/13, Gelucire® 53/10, Gelucire® 62/02, guar gum, hydroxyethyl cellulose, hydroxymethyl cellulose, hydroxypropyl cellulose, hydroxypropyl methylcellulose, magma bentonite, magnesium aluminum silicate, methylcellulose, microcrystalline, non-ionic polysaccharide, pectin, polyethylene oxide, polyvinyl alcohol, polyvinyl alcohol, povidone, propylene glycol alginate, purified bentonite, silicon dioxide, sodium alginate, sodium cellulose, starch, tragacanth, or xanthan gum.

In another embodiment, the matrix fill comprises a viscosity modifier that decreases the viscosity of the matrix fill. Suitable viscosity modifiers include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

Additional pharmaceutical excipients that may be useful for the matrix fills described herein include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and diglycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

In one embodiment described herein, the pharmaceutical composition described herein comprises a soft capsule shell and a matrix fill comprising one or more solubility enhancing agents, one or more viscosity enhancing agents, one or more surfactants, one or more pH modifying agents, one or more active pharmaceutical ingredients, and optionally additional pharmaceutically acceptable excipients.

In one embodiment described herein, the soft capsule matrix fill has the composition of Table 1, including all possible iterations of the specified ranges that provide 100% for the total weight percentage, including or excluding any optional colorings, flavorings, or excipients. In one aspect, the matrix fills described herein are immediate release. In another aspect, the matrix fills described herein are extended release. In another aspect, the matrix fills described herein are controlled release.

TABLE 1

Exemplary Matrix Fill Composition

| Component | Exemplary Components | Composition Range (%) |
|---|---|---|
| Solubility enhancing agent | Polyethylene glycol, Propylene glycol | 40-85 |
| Viscosity enhancing agent | Povidone (K12, K17, K30, K90) | 1-10 |
| pH modifying agent | Citric acid, Tartaric acid, Fumaric acid | 1-3 |
| Surfactant | Sodium lauryl sulfate, Sodium docusate | 1-7 |
| Water | Water | 1-7 |
| Active pharmaceutical ingredient | Fexofenadine HCl | 5-25 |

In one embodiment described herein, the pharmaceutical excipients within the matrix fill described herein reduce or inhibit the activity of the P-glycoprotein efflux transporter (P-gp transporter). In one aspect, this inhibition helps increase the bio absorption of the active pharmaceutical ingredients described herein. Some pharmaceutical excipients harbor P-gp transporter inhibiting activity. In particular, pharmaceutical excipients such as surfactants, polyethylene glycols, solubilizing polymers, and classes of lipids can indirectly reduce or inhibit P-gp transporter activity. Without being bound by any theory, most of these pharmaceutical excipients increase the absorption of putative P-gp substrates by intercalating with the plasma membrane increasing its fluidity or interact with the lipid bi-layer polar headgroups and alter necessary hydrogen bond or ionic forces resulting in the inhibition of the P-gp transporter. Other pharmaceutical excipients inhibit the enzyme ATPase, resulting in acute ATP depletion and subsequent inhibition of the P-gp transporter. See, *Journal of Controlled Release* 90(1): 37-48 (2003) and *Journal of Controlled Release* 130 (2): 98-106 (2000).

In one embodiment described herein, the matrix fill of the pharmaceutical composition comprises one or more solubility enhancing agents comprising from about 40% to about 85% of the matrix fill mass including all iterations of integers within the specified range. In one aspect, the one or more solubility enhancing agents comprises about 50% of the matrix fill mass. In another aspect, the one or more solubility enhancing agents comprises about 68% of the matrix fill mass. In another aspect, the one or more solubility enhancing agents comprises about 74% of the matrix fill mass. In another aspect, the one or more solubility enhancing agents comprises about 84% of the matrix fill mass. In another aspect, the solubility enhancing agent is propylene glycol. In another aspect, the solubility enhancing agent is polyethylene glycol. In another aspect, the solubility enhancing agent is a mixture of polyethylene glycol and propylene glycol.

In one embodiment described herein, the matrix fill of the pharmaceutical composition described herein comprises polyethylene glycol and propylene glycol comprising about 74% of the matrix fill mass.

In one embodiment described herein, the matrix fill of the pharmaceutical composition comprises polyethylene glycol comprising from about 40% to about 75% of the matrix fill mass including all iterations of integers within the specified range. In one aspect, polyethylene glycol comprises about 40% of the matrix fill mass. In another aspect, polyethylene glycol comprises about 50% of the matrix fill mass. In another aspect, polyethylene glycol comprises about 59% of the matrix fill mass. In another aspect, polyethylene glycol comprises about 74% of the matrix fill mass. In another aspect, the polyethylene glycol comprised by the matrix fill has a molecular weight of about 400.

In one embodiment described herein, the matrix fill of the pharmaceutical composition comprises propylene glycol comprising from about 5% to about 25% of the matrix fill mass including all iterations of integers within the specified range. In one aspect, propylene glycol comprises about 5% of the matrix fill mass. In another aspect, propylene glycol comprises about 10% of the matrix fill mass. In another aspect, propylene glycol comprises about 15% of the matrix fill mass. In another aspect, propylene glycol comprises about 20% of the matrix fill mass. In another aspect, propylene glycol comprises about 25% of the matrix fill mass.

In one embodiment described herein, the matrix fill of the pharmaceutical composition comprises a viscosity enhancing agent comprising from about 1% to about 10% of the matrix fill mass including all iterations of integers within the specified range. In one aspect, the viscosity enhancing agent comprises about 1% of the matrix fill mass. In another aspect, the viscosity enhancing agent comprises about 3% of the matrix fill mass. In another aspect, the viscosity enhancing agent comprises about 5% of the matrix fill mass. In another aspect, the viscosity enhancing agent comprises about 6% of the matrix fill mass. In another aspect, the viscosity enhancing agent comprises about 8% of the matrix fill mass. In another aspect, the viscosity enhancing agent comprises about 10% of the matrix fill mass. In another aspect, the viscosity enhancing agent comprises Povidone K90.

In one embodiment described herein, the matrix fill of the pharmaceutical composition comprises one or more pH modifying agents comprising from about 0.5% to about 3% of the matrix fill mass including all iterations of integers within the specified range. In one aspect, the pH modifying agent comprises about 0.5% of the matrix fill mass. In another aspect, the pH modifying agent comprises about 1% of the matrix fill mass. In another aspect, the pH modifying agent comprises about 1.5% of the matrix fill mass. In another aspect, the pH modifying agent comprises about 2% of the matrix fill mass. In another aspect, the pH modifying agent comprises about 2.5% of the matrix fill mass. In another aspect, the pH modifying agent comprises citric acid.

In one embodiment described herein, the matrix fill of the pharmaceutical composition comprises one or more surfactants comprising from about 1% to about 7% of the matrix fill mass including all iterations of integers within the specified range. In one aspect, the surfactant comprises about 1% of the matrix fill mass. In another aspect, the surfactant comprises about 3% of the matrix fill mass. In another aspect, the surfactant comprises about 2.5% of the matrix fill mass. In another aspect, the surfactant comprises about 4% of the matrix fill mass. In another aspect, the surfactant comprises about 7% of the matrix fill mass. In another aspect, the surfactant comprises sodium lauryl sulfate.

In one embodiment described herein, the weight ratio range of polyethylene glycol to propylene glycol in the matrix fill is about 2:1 to about 13:1, including all ratios within the specified range. In one aspect, the weight ratio of polyethylene glycol to propylene glycol in the matrix fill is about 2:1. In another aspect, the weight ratio of polyethylene glycol to propylene glycol in the matrix fill is about 3:1. In another aspect, the weight ratio of polyethylene glycol to propylene glycol in the matrix fill is about 4:1. In another aspect, the weight ratio of polyethylene glycol to propylene glycol in the matrix fill is about 7:1 In another aspect, the weight ratio of polyethylene glycol to propylene glycol in the matrix fill is about 12:1.

In one embodiment described herein, the weight ratio range of surfactant to the one or more solubilizing agents in the matrix fill is about 1:7.5 to about 1:33, including all ratios within the specified range. In one aspect, the weight ratio of surfactant to the one or more solubilizing agents in the matrix fill is about 1:7.5. In another aspect, the weight ratio of surfactant to the one or more solubilizing agents in the matrix fill is about 1:10. In another aspect, the weight ratio of surfactant to the one or more solubilizing agents in the matrix fill is about 1:17.5. In another aspect, the weight ratio of surfactant to the one or more solubilizing agents in the matrix fill is about 1:20. In another aspect, the weight ratio of surfactant to the one or more solubilizing agents in the matrix fill is about 1:34.

In one embodiment described herein, the weight ratio range of viscosity enhancing agent to solubilizing fill (e.g., solubilizing agents, pH modifying agent, and surfactant) in the matrix fill is about 1:6 to about 1:25, including all ratios within the specified range. In one aspect, the weight ratio of viscosity enhancing agent to solubilizing fill in the matrix fill is about 1:6. In another aspect, the weight ratio of viscosity enhancing agent to solubilizing fill in the matrix fill is about 1:13. In another aspect, the weight ratio of viscosity enhancing agent to solubilizing fill in the matrix fill is about 1:15.5. In another aspect, the weight ratio of viscosity enhancing agent to solubilizing fill in the matrix fill is about 1:20. In another aspect, the weight ratio of viscosity enhancing agent to solubilizing fill in the matrix fill is about 1:23.

In one embodiment described herein, polyethylene glycol 400 comprises about 59% of the matrix fill mass, propylene glycol comprises about 15% of the matrix fill mass, Povidone K 90 comprises about 3.3% of the matrix fill mass, citric acid comprises about 1% of the matrix fill mass, sodium lauryl sulfate comprises about 4.2% of the matrix fill mass, the active pharmaceutical ingredient comprises about 15% of the matrix fill mass, and water comprises about 2.5% of the matrix fill mass.

In one embodiment described herein, water comprises about 0.5% to about 5% of the matrix fill mass. In another embodiment described herein, water comprises about 2.5% of the matrix fill mass. In one aspect, the amount of water present in the matrix fill mass is selected to maintain the active pharmaceutical ingredient(s) described herein in solution after encapsulation in the soft capsule shells described herein. In another aspect, the percentage of water comprised by the matrix fill never exceeds more than 10% of the matrix mass.

In one embodiment described herein, the percentage of alcohol is not more than 10% of the matrix fill mass.

In one embodiment a matrix fill as described herein can be manufactured as described below. The surfactant is mixed in water at room temperature in an appropriately sized beaker for the wetting of the surfactant. Next, the one or more solubility enhancing agents and pH modifying agent is added to the mixture at about 65±5° C. and agitated for 45 minutes with an overhead stirrer at about 450 RPM. After a clear solution is formed, the active pharmaceutical ingredient is added slowly while being agitated at about 500 RPM at about 65±5° C. until the active pharmaceutical ingredient is completely solubilized. Next, the viscosity enhancing agent is added slowly and stirred at about 500 RPM at about 65±5° C. until the viscosity enhancing agent is solubilized completely. The formulation is then filtered through a 35 micron filter cloth and vacuum degassed. In addition to the above mentioned conditions, a wide range of temperatures and stirring speeds can be applied to achieve a clear solution of the matrix fill.

In one embodiment described herein, the pharmaceutical composition comprises a soft capsule shell comprising a matrix comprising an active pharmaceutical ingredient.

In one embodiment described herein, the soft capsule shell has the composition of Table 2, including all possible iterations of the specified ranges that provide 100% for the total weight percentage, including or excluding the optional colorings, flavorings, or excipients.

TABLE 2

Exemplary soft gelatin capsule composition

| Component | Exemplary Component | Weight Percentage (%) |
| --- | --- | --- |
| Film-forming polymer | Gelatin | 25-50 |
| Plasticizer | Glycerol | 15-25 |
| pH modifier | Citric acid | 0.5-2 |
| Solvent | Water | 20-40 |
| Opacifier (optional) | Titanium dioxide | 0.5-1.5 |
| Coloring agent (optional) | Various | 0.05-0.1% |

Film-former polymers that are useful for creating soft capsules as described herein are gelatin or hydroxypropylmethylcellulose (HPMC). In one aspect, the film-forming polymer is gelatin.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 3.

TABLE 3

Exemplary Soft Capsule Shell Composition

| Component | Percent weight (%) |
| --- | --- |
| Gelatin | 43 |
| Glycerol | 20 |
| Titanium dioxide | 0.7 |
| Coloring agent | 0.1 |
| Citric acid | 1.0 |
| Water | 35.2 |
| TOTAL | 100% |
| Final pH | 4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 1% citric acid, about 35% water; optionally, about 0.7% titanium dioxide; and optionally, about 0.1% of at least one coloring agent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming 1 polymer weight percentage is about 42%. In another aspect, the film-forming polymer weight percentage is about 44%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one embodiment, the soft capsule shell mass comprises a pH modifier as to reduce crosslinking with the soft capsule shell and reduce the dissolution rates of the active pharmaceutical ingredients described herein. In one aspect, the pH modifier is citric acid.

In one embodiment, the weight percentage range of citric acid in the soft capsule shell described herein is about 0.5% to about 2%, including all integers within the specified range. In one aspect, the weight percentage of citric acid in the soft capsule shell is about 0.5%. In another aspect, the weight percentage of citric acid in the soft capsule shell is about 1%. In another aspect, the weight percentage of citric acid in the soft capsule shell is about 1.5%. In another aspect, the weight percentage of citric acid in the soft capsule shell is about 2.0%.

In one aspect, soft capsules are made using a rotary die apparatus as described in U.S. Pat. Nos. 5,459,983; 5,146,730; and 6,482,516, each of which are incorporated by reference herein for such teachings.

In one embodiment, the soft capsule shell mass is clear or transparent. In one aspect, the soft capsule shell mass is clear or transparent and comprises the matrix fill that is clear or transparent as described herein. In another aspect, the soft capsule shell mass is colored and comprises the matrix fill that is clear or transparent as described herein. In another aspect, the soft capsule shell mass is opaque and comprises the matrix fill that is clear or transparent as described herein.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658 and U.S. Patent Application Publication No. US 2006/0165778, both of which are incorporated by reference herein for such teachings. The enteric soft capsule shell can comprise one or more film forming polymers, one or more enteric acid insoluble polymers, one or more plasticizers, one or more alkali neutralizing agents, one or more solvents, optionally one or more colorants, and optionally one or more flavorings and/or other conventionally accepted pharmaceutical excipients or additives.

Film-former polymers that are useful for creating enteric soft capsules are gelatin or hydroxypropylmethylcellulose (HPMC). In one aspect of the enteric soft capsule shell described herein, the film-forming polymer is gelatin.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacrylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 4, including all possible iterations of the specified ranges that provide 100% for the total weight percentage, including or excluding the optional, excipients, opacifiers, colorants, and flavorings.

TABLE 4

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| pH modifier | Citric acid | 0.5-2 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer; about 10% enteric, acid insoluble polymer; about 20% plasticizer; about 1% alkali neutralizing agent; about 1% of a pH modifier; and about 37% solvent.

In one embodiment, the weight percentage range of total polymer content (i.e., film forming polymer and enteric acid-insoluble polymer) of the enteric soft capsule described herein is about 30% to about 45%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all iterations of integers within the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the enteric soft capsule shell mass comprises a pH modifier as to reduce crosslinking with the soft capsule shell and reduce the dissolution rates of the active pharmaceutical ingredients described herein. In one aspect, the pH modifier is citric acid.

In one embodiment, the weight percentage range of citric acid in the enteric soft capsule shell described herein is about 0.5% to about 2%, including all integers within the specified range. In one aspect, the weight percentage of citric acid in the enteric soft capsule shell is about 0.5%. In another aspect, the weight percentage of citric acid in the enteric soft capsule shell is about 1%. In another aspect, the weight percentage of citric acid in the enteric soft capsule shell is about 1.5%. In another aspect, the weight percentage of citric acid in the enteric soft capsule shell is about 2.0%.

In one embodiment, the weight ratio range of film forming polymer to enteric acid insoluble polymer (film forming: enteric) is about 25:75 ($\approx$0.33) to about 40:60 ($\approx$0.67) (i.e., $\approx$0.33-0.67), including all iterations of ratios within the specified range. In one aspect, the ratio of film forming polymer to enteric acid insoluble polymer is about 30:70 ($\approx$0.43). In another aspect, the ratio of film forming polymer to enteric acid insoluble polymer is about 28:72 ($\approx$0.38).

In one embodiment, the weight ratio of total plasticizer to film forming polymer is about 20:40 to 21:30 (i.e., $\approx$0.5-0.7), including all iterations of ratios within the specified range. In one aspect, the weight ratio of total plasticizer to film forming polymer is about 20:40 ($\approx$4.5). In another aspect, the weight ratio of total plasticizer to film forming polymer is about 21:30 ($\approx$0.7). In another aspect, the weight ratio of total plasticizer to film forming polymer is about 19:29 ($\approx$0.65). In another aspect, the weight ratio of total plasticizer to film forming polymer is about 19.3:29.2 ($\approx$0.66).

In one embodiment, the weight ratio of total plasticizer to enteric acid insoluble polymer is about 1:1 to about 2:1 ($\approx$1-2), including all iterations of ratios within the specified range. In one aspect, the weight ratio of total plasticizer to enteric acid insoluble polymer is about 11:10 ($\approx$1.1). In another aspect, the weight ratio of total plasticizer to enteric acid insoluble polymer is about 14:10 ($\approx$1.4). In another aspect, the weight ratio of total plasticizer to enteric acid insoluble polymer is about 17:10 ($\approx$1.7). In another aspect, the weight ratio of total plasticizer to enteric acid insoluble polymer is about 20:10 ($\approx$2). In another aspect, the weight ratio of total plasticizer to enteric acid insoluble polymer is about 19.3:11.2 ($\approx$21.73).

In one embodiment, the weight ratio range of total plasticizer to total polymer (film forming and enteric acid insoluble polymer) is about 18:45 to about 20:40 (i.e., ≈0.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 5.

TABLE 5

Exemplary Enteric Soft Capsule Shell Composition

| Component | Percent weight |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Citric acid | 1.0 |
| Titanium dioxide | 1.5 |
| Water | 37.1 |
| TOTAL | 100% |
| Final pH | 4-7 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ≈ribbons that form the enteric capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment, the composition described herein can provide a dosage of an active ingredient for administration. The dosage form can be administered, for example, to a subject, or a subject in need thereof. In one aspect, the subject may be a mammal, or a mammal in need thereof. In another aspect, the dosage form can be administered, for example, to a human or a human in need thereof. In another aspect, the human subject or a human subject in need thereof is a medical patient.

One embodiment described herein is a pharmaceutical composition comprising a soft capsule as described herein comprising an active pharmaceutical ingredient or plurality of active pharmaceutical ingredients. In one aspect, the active pharmaceutical ingredient is a BCS class II compound. In another aspect, the active pharmaceutical ingredient is a BCS class III compound. In another aspect, the active pharmaceutical ingredient is a BCS class IV compound.

In one embodiment, the active pharmaceutical ingredient is a compound that has a minimal solubility in water for which delivery is desired. The compounds may be sparingly soluble, slightly soluble, very slightly soluble, or insoluble in water. The following list of active pharmaceutical ingredients is suitable for delivery in the matrix fills described herein. A person of skill in the art would recognize additional suitable active pharmaceutical ingredients not provided herein. Non-limiting examples of such active agents would include acyclovir, acrivastine, adriamycin, albendazole, albuterol, amlodipine, amphetamine, amphotericin B, angiotensin converting enzyme (ACE) or NEP inhibitors, atorvastatin, atovaquone, azithromycin, baclofen, bicalutamide, busulfan, butenafine, calcipotriene, calcitriol, camptothecin, cannabinoids, capsaicin, carbamazepine, carotenes, celecoxib, cerivastatin, cetirizine, chlorpheniramine, cimetidine, ciprofloxacin, cisapride, clarithromycin, clemastine, codeine, cyclosporin, danazol, dantrolene, dexchlorpheniramine, digoxin, dirithromycin, donepezil, efavirenz, eprosartan and other sartans, ergotamines, esomeprazole, estrogens, etodolac, etoposide, famotidine, fenofibrate, fibric acid derivatives, fentanyl, fexofenadine, finasteride, fluconazole, flurbiprofen, flutamide, fluvastatin, fosphenytoin, frovatriptan, gabapentin, gemfibrozil, glibenclamide, glimepiride, glipizide, glyburide, griseofulvin, halofantrine, ibuprofen, pralnacasan, indomethacin, irinotecan, isotretinoin, isradipine, itraconazole, ivermectin, ketoconazole, ketorolac, lamotrigine, lansoprazole, leflunomide, loperamide, loratadine, lovastatin, lycopenes, mefloquine, melphalan, methadone, methoxsalen, metronidazole, miconazole, midazolam, mifepristone, miglitol, mitoxantrone, nabumetone, nalbuphine, naproxen, naratriptan, nelfinavir, nifedipine, nilutamide, nizatidine, omeprazole, oxaprozin, oxcarbazepine, paclitaxel, pentazocine, phenytoin, pioglitazone, pizotifen, pralnacasan, pravastatin, probucol, lansoprazole, pseudoephedrine, pyridostigmine, rabeprazole, raloxifene, repaglinide, rifapentine, rimexolone, rizatriptan, rofecoxib, rosiglitazone, saquinavir, sibutramine, sildenafil citrate, simvastatin, sirolimus, spironolactone, steroids, sumatriptan, tacrine, tacrolimus, tamoxifen, tamsulosin, targretin, tazarotene, teniposide, terbinafine, testosterones, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zileuton, zolmitriptan, zolpidem, zopiclone, or pharmaceutically acceptable salts, isomers, prodrugs (e.g., esters) and derivatives thereof, and mixtures of any of the active pharmaceutical ingredients listed thereof.

In another embodiment, the active pharmaceutical ingredient can be a compound that is poorly soluble or has a low solubility (e.g., any BCS class II or BCS class IV compound). Exemplary compounds include but are not limited to: aceclofenac, acetaminophen (i.e., paracetamol), acetazolamide, acetylsalicylic acid, acrivastine, acyclovir, albendazole, allopurinol, aluminium hydroxide, amoxicillin, atorvastatin, azathioprine, azelastine, azithromycin, benidipine, bicalutamide, bisacodyl, cabergoline, candesartan cilexetil, carbamazepine, carvedilol, cefdinir, cefditoren pivoxil, cefixime, cefotiam hexetil hydrochloride, cefpodoxime proxetil, cefuroxime axetil, celecoxib, cetirizine, chloroquine, chlorpromazine, cilostazol, clarithromycin, clofazimine, clopidogrel, clozapine, cyclosporine, cyproterone, dapsone, dexamethasone, diazepam, diclofenac, diloxanide, doxycycline, ebastine, efavirenz, epalrestat, eprosartan, erythromycin ethylsuccinate, ethyl icosapentate, ezetimibe, famotidine, fenofibrate, fexofenadine, flurbiprofen, folic acid, furosemide, gefitinib, gliclazide, glimepiride, glipizide, glyburide(glibenclamide), griseofulvin, haloperidol, hydrochlorothiazide, hydroxyzine, ibuprofen, imatinib, indinavir, iopanoic acid, irbesartan, isotretinoin, itraconazole, ivermectin, ketoprofen, lamotrigine, l-carbocysteine, levodopa, levosulpiride, linezolid, lopinavir, loratadine, lorazepam, lovastatin, manidipine, mebendazole, medroxyprogesterone, meloxicam, menatetrenone, mesalamine, metaxalone, methylphenidate, metoclopramide, metronidazole, modafinil, mosapride, mycophenolate mofetil, nabumetone, nalidixic acid, nelfinavir, nevirapine, nicergoline, niclosamide, nifedipine, nilvadipine, nimesulide, nitrofurantoin, nystatin, olanzapine, orlistat, oxcarbazepine, oxycodone, phenobarbital, phenytoin, pioglitazone, pranlukast, praziquantel, propylthiouracil, pyrantel, pyrimethamine, quetiapine, quinine, raloxifene, rebamipide, retinol, rifampicin, risperidone, ritonavir, rofecoxib, roxithromycin, sennosides, simvastatin, spironolactone, sulfadiazine, sulfamethoxazole, sulfasalazine, sultamicillin, tacrolimus, tamoxifen, telmisartan, teprenone, theophylline, ticlopidine, tocopherol nicotinate, tosufloxacin, triflusal, trimethoprim, ursodeoxycholic acid, valproic acid, valsartan, verapamil, warfarin, and zaltoprofen or pharmaceutically acceptable salts, isomers, prodrugs (e.g., esters) and derivatives thereof, and mixtures of any of the active pharmaceutical ingredients listed thereof.

In another embodiment, the active pharmaceutical ingredient can be a compound that is poorly soluble or has a low solubility and has a low permeability (e.g., any BCS class IV compound). Exemplary compounds include but are not limited to acetaminophen, acetazolamide, acyclovir, allopurinol, amoxicillin, cefdinir, cefixime, cefotiam hexetil hydrochloride, cefpodoxime proxetil, cefuroxime axetil, dapsone, dexamethasone, doxycycline, famotidine, fexofenadine, folic acid, furosemide, glipizide, griseofulvin, hydrochlorothiazide, l-carbocysteine, levodopa, levosulpiride, linezolid, meloxicam, mesalamine, metoclopramide, modafinil, nabumetone, nalidixic acid, oxcarbazepine, oxycodone, phenobarbital, propylthiouracil, sulfadiazine, sulfamethoxazole, sultamicillin, theophylline, tosufloxacin, triflusal, trimethoprim, and zaltoprofen or pharmaceutically acceptable salts, isomers, prodrugs (e.g., esters) and derivatives thereof, and mixtures of any of the active pharmaceutical ingredients listed thereof.

Another embodiment described herein is a method for treating, ameliorating the symptoms of, or delaying the onset of a medical condition by providing a subject in need thereof with a pharmaceutical composition comprising a soft capsule, as described herein, comprising a pharmaceutical ingredient or ingredients. As used herein, a medical condition can comprise any actual or suspected disease, disorder, or condition that a subject may seek medical care therefor. One embodiment described herein is method of treating, ameliorating the symptoms of, or delaying the onset of a medical condition of includes administering a pharmaceutical ingredient having a desired therapeutic or biological activity or suspected of having a desired therapeutic or biological activity in a subject in need thereof.

In one embodiment described herein, an active pharmaceutical ingredient is the only active ingredient in the pharmaceutical composition. In another embodiment, the active ingredient or drug can be an active pharmaceutical ingredient, derivatives thereof, or combinations thereof.

In one embodiment, the pharmaceutical compositions as described herein are suitable for the delivery of poorly soluble compounds or compounds having a low solubility in water. In another embodiment, the pharmaceutical compositions as described herein are suitable for the delivery of compounds that are also insoluble in oil or lipophilic carriers.

In another embodiment, the pharmaceutical compositions described herein may comprise pharmaceutically acceptable salts of any of the above mentioned active drug substances. The term "pharmaceutically acceptable salts" of an active pharmaceutical ingredient includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, or toluenesulphonic acid, etc. In another embodiment, the active pharmaceutical ingredient may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the active pharmaceutical ingredient may be in any of its crystalline, polymorphous, semicrystalline, amorphous or polymorphous forms or mixtures thereof.

In one embodiment described herein, the ratio of the active ingredient or drug to the matrix fill (only the matrix fill ingredients, e.g., the solubility and viscosity enhancing agents, pH modifying agent(s), surfactant(s), and water) can be from about 1:20 to about 1:2 by weight, including all ratios in the specified range. In one aspect, the active ingredient to total matrix fill ratio can also be about 1:19; about 1:9; about 1:4; about 1:3; or about 1:2. In another aspect described herein, the active ingredient to total matrix fill ratio can be about 1:5.6 by weight.

In another embodiment described herein, the ratio of the active ingredient or drug to the total mass of the matrix fill (e.g., all matrix fill ingredients including the active pharmaceutical ingredient) can be from about 1:20 to about 1:3 by weight, including all ratios in the specified range. In one aspect, the active ingredient to total matrix fill ratio can also be about 1:19; about 1:9; about 1:6; or about 1:3. In another aspect described herein, the active ingredient to total matrix fill ratio can be about 1:6.7 by weight.

In one embodiment described herein, the active ingredient or drug comprises from about 5% to about 80% of the matrix fill mass including all iterations of integers within the specified range. In another embodiment described herein, the active ingredient or drug comprises from about 5% to about 50% of the matrix fill mass including all iterations of integers within the specified range. In another embodiment described herein, the active ingredient or drug comprises from about 5% to about 25% of the matrix fill mass including all iterations of integers within the specified range. In one aspect described herein, the active ingredient or drug comprises about 25% of the matrix fill mass. In another aspect, the active ingredient or drug comprises about 20% of the matrix fill mass. In another aspect, the active ingredient or drug comprises about 15% of the matrix fill mass. In another aspect, the active ingredient or drug comprises about 10% of the matrix fill mass. In another aspect, the active ingredient or drug comprises about 5% of the matrix fill mass.

In another embodiment described herein, the active ingredient or drug comprises about 80%, about 70%, about 60%, about 50%, about 40%, about 30%, about 20%; about 15%; about 10%; about 5%; about 2%, or about 1% of the matrix fill mass.

In one embodiment, the pharmaceutical composition described herein comprises an active pharmaceutical ingredient of about 10 mg to about 1000 mg, including all iterations of integers within the specified range. In one aspect, the pharmaceutical composition described herein, comprises an active pharmaceutical ingredient in the range of about 10 mg to about 100 mg, including all iterations of integers within the specified range. In another aspect, the pharmaceutical composition described herein, comprises an active pharmaceutical ingredient in the range of about 100 mg to about 250 mg, including all iterations of integers within the specified range. In another aspect, the pharmaceutical composition described herein, comprises an active pharmaceutical ingredient in the range of about 250 mg to about 500 mg, including all iterations of integers within the specified range. In another aspect, the pharmaceutical composition described herein, comprises an active pharmaceutical ingredient in the range of about 500 mg to about 750 mg, including all iterations of integers within the specified range. In another aspect, the pharmaceutical composition described herein, comprises an active pharmaceutical ingredient in the range of about 750 mg to about 1000 mg, including all iterations of integers within the specified range.

In another embodiment, the pharmaceutical composition described herein comprises an active pharmaceutical ingredient described herein of at least about 10 mg, at least about 20 mg, at least about 30 mg, at least about 40 mg, at least about 50 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 210 mg, at least about 220 mg, at least about 230 mg, at least about 240 mg, at least about 250 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg, or at least about 1000 mg.

The concentration or dose of the active pharmaceutical ingredient in the pharmaceutical composition depends on the specific active pharmaceutical ingredient, the disease to be treated, the condition of the patient, the age, and gender of the patient, etc. The active pharmaceutical ingredient may be a well-known active pharmaceutical ingredient and a person having ordinary skill in the art will be able to find information as to the dosage of each active drug substance and, accordingly, will know how to determine the amount of each active drug substance in the pharmaceutical composition.

In one embodiment described herein, the soft capsules described herein comprises an anti-allergenic active pharmaceutical ingredient.

In one embodiment described herein, the soft capsules described herein comprise an active pharmaceutical ingredient comprising fexofenadine or a pharmaceutically acceptable salt form thereof, including but not limited to fexofenadine sodium, fexofenadine potassium, or fexofenadine hydrochloride. In another embodiment, fexofenadine is present in its free acid form. In another embodiment fexofenadine is present as fexofenadine hydrochloride (i.e., fexofenadine HCl). As used herein, "fexofenadine" refers all possible salt forms or free acid forms of the active pharmaceutical ingredient, if a particular salt is not specified.

In one embodiment described herein, the soft capsules comprising the matrix fill described herein are optically clear or transparent. In one aspect, the soft capsules comprising the matrix fill described herein further comprising fexofenadine are optically clear or transparent. In another aspect, the matrix fill described herein further comprising fexofenadine are clear or transparent but colored.

In one embodiment described herein, fexofenadine comprises about 5% to about 35% by weight of the total matrix fill mass. In one aspect described herein, fexofenadine comprises about 5% by weight of the matrix fill mass. In another aspect described herein, fexofenadine comprises about 10% by weight of the matrix fill mass. In another aspect described herein, fexofenadine comprises about 15% by weight of the matrix fill mass. In another aspect described herein, fexofenadine comprises about 20% by weight of the matrix fill mass. In another aspect described herein, fexofenadine comprises about 25% by weight of the matrix fill mass. In another aspect described herein, fexofenadine comprises about 35% by weight of the matrix fill mass.

In one embodiment described herein, the dose of fexofenadine is about 10 mg to about 500 mg, including all integers within the specified range. In one aspect, the dose of fexofenadine is about 10 mg. In another aspect, the dose of fexofenadine is about 12.5 mg. In another aspect, the dose of fexofenadine is about 25 mg. In another aspect, the dose of fexofenadine is about 50 mg. In another aspect, the dose of fexofenadine is about 75 mg. In another aspect, the dose of fexofenadine is about 100 mg. In another aspect, the dose of fexofenadine is about 125 mg. In another aspect, the dose of fexofenadine is about 150 mg. In another aspect, the dose of fexofenadine is about 180 mg. In another aspect, the dose of fexofenadine is about 200 mg. In another aspect, the dose of fexofenadine is about 225 mg. In another aspect, the dose of fexofenadine is about 250 mg. In another aspect, the dose of fexofenadine is about 300 mg. In another aspect, the dose of fexofenadine is about 350 mg. In another aspect, the dose of fexofenadine is about 400 mg. In another aspect, the dose of fexofenadine is about 450 mg. In another aspect, the dose of fexofenadine is about 500 mg.

In one embodiment, the dosage can contain an amount of fexofenadine effective for treatment, amelioration, prophylaxis, or reducing the onset of or symptoms of mild, moderate, or severe seasonal allergic rhinitis.

In another embodiment, the dosage can contain an amount of fexofenadine effective for treatment, amelioration, prophylaxis, or reducing the onset of or symptoms of mild, moderate, or severe sneezing stemming from seasonal allergic rhinitis.

In another embodiment, the dosage can contain an amount of fexofenadine effective for treatment, amelioration, prophylaxis, or reducing the onset of or symptoms of mild, moderate, or severe rhinorrhea stemming from seasonal allergic rhinitis.

In another embodiment, the dosage can contain an amount of fexofenadine effective for treatment, amelioration, prophylaxis, or reducing the onset of or symptoms of mild, moderate, or severe itchy nose stemming from seasonal allergic rhinitis.

In another embodiment, the dosage can contain an amount of fexofenadine effective for treatment, amelioration, prophylaxis, or reducing the onset of or symptoms of mild, moderate, or severe itchy palate stemming from seasonal allergic rhinitis.

In another embodiment, the dosage can contain an amount of fexofenadine effective for treatment, amelioration, prophylaxis, or reducing the onset of or symptoms of mild, moderate, or severe itchy throat stemming from seasonal allergic rhinitis.

In another embodiment, the dosage can contain an amount of fexofenadine effective for treatment, amelioration, prophylaxis, or reducing the onset of or symptoms of mild, moderate, or severe itchy eyes stemming from seasonal allergic rhinitis.

In another embodiment, the dosage can contain an amount of fexofenadine effective for treatment, amelioration, prophylaxis, or reducing the onset of or symptoms of mild, moderate, or severe watery eyes stemming from seasonal allergic rhinitis.

In another embodiment, the dosage can contain an amount of fexofenadine effective for treatment, amelioration, prophylaxis, or reducing the onset of or symptoms of chronic idiopathic urticaria.

In another embodiment, the dosage can contain an amount of fexofenadine effective for treatment, amelioration, prophylaxis, or reducing the onset of or symptoms of pruritus and the number of wheals stemming from chronic idiopathic urticaria.

Without being bound to any theory, the primary mechanism thought to be responsible for fexofenadine's effects on reducing allergic rhinitis is through the inhibition of histamine release from mast cells. Fexofenadine is a selective peripheral $H_1$ receptor antagonist and functions irrespective of its enantiomeric form. Further, fexofenadine hydrochloride is unable to cross the blood-brain barrier.

In one embodiment, the total dosage of fexofenadine administered in a 24-hour period is about 20 mg to about 1000 mg per 24-hour period including all iterations of integers within the specified range. In another embodiment, the total dosage of fexofenadine administered in a 24-hour period is about 50 mg to about 250 mg per 24-hour period including all iterations of integers within the specified range. In one aspect, the total dosage of fexofenadine administered in a 24-hour period is about 50 mg. In another aspect, the total dosage of fexofenadine administered in a 24-hour period is about 100 mg. In another aspect, the total dosage of fexofenadine administered in a 24-hour period is about 150 mg. In another aspect, the total dosage of fexofenadine administered in a 24-hour period is about 200 mg. In another aspect, the total dosage of fexofenadine administered in a 24-hour period is about 250 mg. In another aspect, the total dosage of fexofenadine administered in a 24-hour period is about 500 mg. In another aspect, the total dosage of fexofenadine administered in a 24-hour period is about 750 mg. In another aspect, the total dosage of fexofenadine administered in a 24-hour period is about 1000 mg.

In another embodiment, the total dosage of fexofenadine administered in a 24-hour period is about 60 mg, or about 120 mg, or about 180 mg and is effective for the treatment of seasonal allergic rhinitis administered in equal daily doses (i.e., 60 mg once per day; 60 mg 2 or 3 times daily; or 180 mg once per day, or combinations thereof to reach a desired therapeutic efficacy).

In another embodiment, the total dosage of fexofenadine administered in a 24-hour period is about 60 mg or about 120 mg and is effective for the treatment of chronic idiopathic urticaria administered in equal daily doses (i.e., 60 mg once per day or 60 mg twice per day).

The dosage form can be administered, for example, 1×, 2×, 3×, 4×, 5×, 6×, 7×, or 8×, per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, or even longer. One or more dosage forms can be administered until the patient, subject, mammal, mammal in need thereof, human, or human in need thereof, does not require treatment, prophylaxis, or amelioration of any disease or condition such as, for example, seasonal allergic rhinitis or chronic idiopathic urticaria.

In another embodiment described herein, the total mass of the matrix fill of the pharmaceutical composition described herein that comprises an active pharmaceutical ingredient described herein is from about 100 mg to about 1600 mg. In one aspect, the total mass of the matrix fill mass is about 200 mg. In another aspect, the total mass of the matrix fill mass is about 400 mg. In one aspect, the total mass of the matrix fill mass is about 800 mg. In another aspect, the total mass of the matrix fill mass is about 1200 mg.

In another embodiment described herein, the pharmaceutical composition comprises 30 mg of fexofenadine in a total matrix fill mass of 200 mg. In another embodiment described herein, the pharmaceutical composition comprises 60 mg of fexofenadine in a total matrix fill mass of 400 mg. In another embodiment described herein, the pharmaceutical composition comprises 120 mg of fexofenadine in a total matrix fill mass of 800 mg. In another embodiment described herein, the pharmaceutical composition comprises 180 mg of fexofenadine in a total matrix fill mass of 1200 mg.

In one embodiment described herein, the soft capsules described herein comprises a matrix fill having controlled, delayed, or extended release properties. Such controlled or extended release matrix fills are described in International Patent Application Publication No. WO 2005/009409 and U.S. Patent Application Publication No. US 2006/0115527, both of which are incorporated by reference herein for such teachings. In one aspect, the matrix fill can be configured to provide immediate release, controlled release, extended release, sustained release, delayed release, or combinations thereof.

Accordingly, one embodiment described herein is a controlled release soft capsule having a shell and a matrix fill, wherein the matrix fill includes an active pharmaceutical ingredient.

The liquid active ingredients can be prepared to contain the active pharmaceutical ingredient in the range of 0.005% to 100%, including all iterations of integers with the specified range, with the balance made up from non-toxic carrier. Methods for preparation of these compositions are known to those skilled in the art. See, for example, *Remington's Pharmaceutical Sciences*, Mack Publishing Company, Easton, Pa., 15$^{th}$ Edition, 1975. The liquid portion of the matrix fill can contain 0.001% to 100%, 0.1% to 95%, 1% to 90%, 5% to 70%, or 10% to 50% by weight active ingredient.

In another embodiment described herein, the oral pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

In one aspect, the pharmaceutical compositions described herein are stable at 25° C. and 60% relative humidity (RH) for at least about 1 month, at least about 2 months, at least about 3 months, at least about 4 months, at least about 5 months, at least about 6 months, at least about 9 months, at least about 10 months, at least about 11 months, at least about 12 months, or even longer. In another aspect, the pharmaceutical compositions described herein are stable for 1 year or longer at 25° C. and 60% RH. In another aspect, the pharmaceutical compositions described herein are stable for 2 years or longer at 25° C. and 60% RH.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the specified embodiments. All of the various embodiments, aspects, and options disclosed herein can be combined in all variations. The scope of the compositions, formulations, methods, and processes described herein include all actual or potential combinations of embodiments, aspects, options, examples, and preferences herein described. All patents and publications cited herein are incorporated by reference herein for the specific teachings thereof.

EXAMPLES

Example 1

Manufacturing Process

In one embodiment a matrix fill as described herein can be manufactured as described below. Sodium lauryl sulfate is mixed in water at room temperature in an appropriately sized beaker for the wetting of the surfactant. Proper wetting of sodium lauryl sulfate reduces processing time. Next, polyethylene glycol 400, propylene glycol, and citric acid is added to the mixture at about 65±5° C. and agitated for 45 minutes with an overhead stirrer at about 450 RPM. After a clear solution is formed, the fexofenadine HCl is added slowly while being agitated at about 500 RPM at about 65±5° C. until it is completely solubilized. Next, the povidone K 90 is added slowly and stirred at about 500 RPM at about 65±5° C. until it is solubilized completely. The clear formulation is then filtered through a 35 micron filter cloth and vacuum degassed.

Example 2

Examples of gel mass compositions useful for producing gelatin enteric soft capsules are shown below in Table 6. Composition components are set forth by weight percentage of the total weight of the matrix fill mass.

TABLE 6

Exemplary Matrix Fill Compositions

| Ingredient | Weight Percentage (%) | | | | | |
|---|---|---|---|---|---|---|
| | EX 1 | EX 2 | EX 3 | EX 4 | EX 5 | EX 6 |
| Polyethylene glycol (PEG) | 49 | 40 | 74 | 63 | 55 | 52 |
| Propylene glycol (PG) | 23 | 12 | 10 | 5 | 15 | 22 |
| pH modifying agent | 1.5 | 2 | 2.5 | 1 | 1.5 | 1 |
| Surfactant | 7 | 7 | 2.5 | 4.5 | 6 | 5 |
| Viscosity enhancing agent | 6 | 10 | 4 | 3.5 | 5 | 1 |
| Active pharmaceutical ingredient | 10 | 25 | 5 | 20 | 15 | 15 |
| Water | 3.5 | 4 | 2 | 3 | 2.5 | 4 |
| TOTAL | 100 | 100 | 100 | 100 | 100 | 100 |
| Components and Relational Ratios | | | | | | |
| Total solubility enhancing agents (PEG + PG) | 72 | 52 | 84 | 68 | 70 | 74 |
| Ratio of PEG to PG | 2.1 | 3.3 | 7.4 | 12.6 | 3.7 | 2.4 |
| Ratio of surfactant to solubility enhancing agents (PEG + PG) | 0.10 | 0.13 | 0.03 | 0.07 | 0.09 | 0.07 |
| Ratio of viscosity enhancing agent to solubility enhancing agent (PEG + PG) | 0.10 | 0.15 | 0.05 | 0.04 | 0.07 | 0.01 |
| Ratio of active pharmaceutical ingredient to total fill | 0.1 | 0.25 | 0.05 | 0.2 | 0.15 | 0.15 |

Example 3

Examples of gel mass compositions useful for producing gelatin enteric soft capsules are shown below in Table 7. Composition components are set forth by weight in milligrams.

TABLE 7

Exemplary Matrix Fill Compositions

| Ingredient | Weight (mg) | | | | | |
|---|---|---|---|---|---|---|
| | EX 1 | EX 2 | EX 3 | EX 4 | EX 5 | EX 6 |
| Polyethylene glycol (PEG) | 44.3 | 118 | 236 | 472 | 708 | 944 |
| Propylene glycol (PG) | 11.3 | 30 | 60 | 120 | 180 | 240 |
| pH modifying agent | 0.8 | 2 | 4 | 8 | 12 | 16 |
| Surfactant | 3.1 | 8.3 | 16.7 | 33.4 | 50 | 66.7 |
| Viscosity enhancing agent | 2.5 | 6.7 | 13.3 | 26.6 | 40 | 53.3 |
| Active pharmaceutical ingredient | 11.3 | 30 | 60 | 120 | 180 | 240 |
| Water | 1.9 | 5 | 10 | 20 | 30 | 40 |
| TOTAL | 75 | 200 | 400 | 800 | 1200 | 1600 |

Example 4

Matrix fill compositions were prepared according to the composition shown in Table 8 and were encapsulated in a soft gelatin capsule. Matrix fills were physically and chemically stable after three months with no crosslinking of the soft capsule shell. Optical microscopy, moisture analysis and pH measurements of the matrix fill before and after encapsulation, hardness, assay, degradation and dissolution studies were carried out successfully under ICH stability conditions (25° C., 60% RH; 30° C., 65% RH; 40° C., 75% RH). The soft gelatin dosage form was determined to be stable and performed in accordance with requirements of a soft gelatin dose form.

Figure 2:
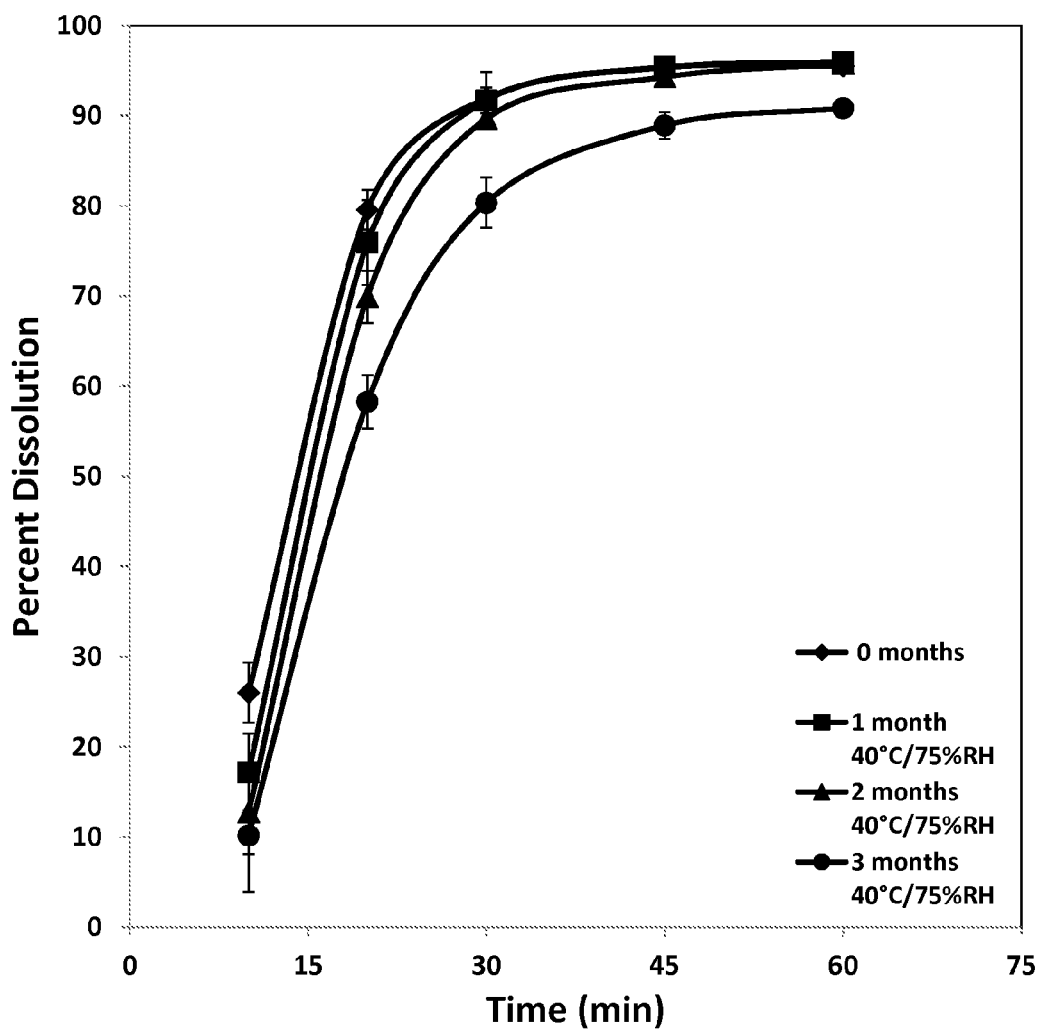
FIG. 2. Dissolution kinetics of soft gelatin capsules with 180 mg fexofenadine HCl matrix fills after different storage times.
Figure 3:
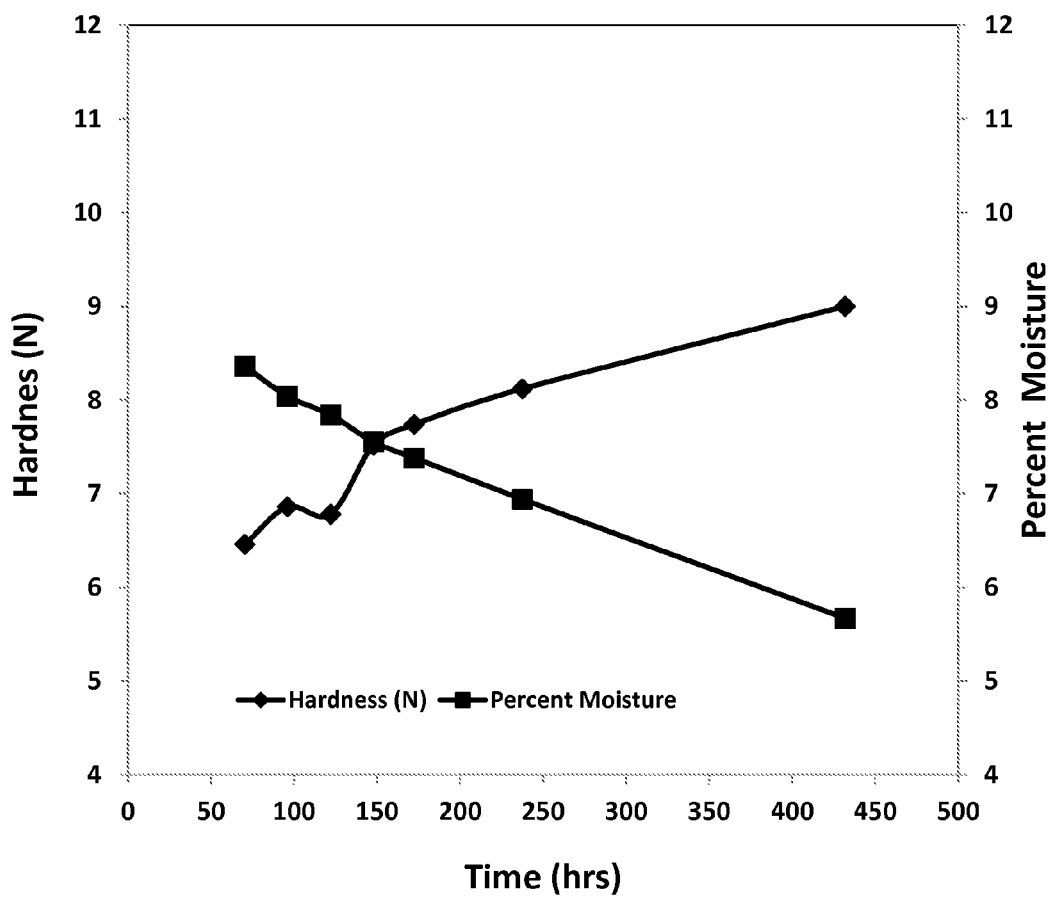
FIG. 3. Hardness and moisture results of the soft gelatin capsules with 180 mg fexofenadine HCl matrix fills after drying.

The dissolution kinetics of the soft gelatin capsules comprising the matrix fills shown in Table 8 were tested under USP test 3 conditions in an appropriate dissolution media (0.001 N HCl). Assessment of active release (fexofenadine) was determined by HPLC analysis. The capsules comprising the matrix fill composition shown in Table 8 were tested immediately and compared to a commercially available fexofenadine formulation following encapsulation (0 months) or after storage for 3 months at 25° C., 60% RH and 6 months at 30° C., 65% RH (FIG. 1). The capsules comprising the matrix fill composition shown in Table 8 were further tested after storage for 1 month at 40° C., 75% RH, 2 months at 40° C., 75% RH, and 3 months at 40° C., 75% RH (FIG. 2). The capsules comprising the matrix fill composition in Table 8 were tested for their hardness and moisture content after drying (FIG. 3). The capsules, by day 10 of drying (237 hours), had a burst strength of 33.4 kg and an elasticity of 3.8 mm (n=6 capsules tested).

TABLE 8

Matrix Fill Compositions

| Ingredients | Weight (%) | Weight (mg/cap) | Weight (g/batch) |
|---|---|---|---|
| Polyethylene glycol (PEG) | 59 | 708 | 442.5 |
| Propylene glycol (PG) | 15 | 180 | 112.5 |

TABLE 8-continued

Matrix Fill Compositions

| Ingredients | Weight (%) | Weight (mg/cap) | Weight (g/batch) |
|---|---|---|---|
| Citric acid | 1 | 12 | 7.5 |
| Sodium lauryl sulfate | 4.2 | 50 | 31.3 |
| Povidone K90 | 3.3 | 40 | 25 |
| Fexofenadine HCl | 15 | 180 | 112.5 |
| Water | 2.5 | 30 | 18.8 |
| TOTAL | 100 | 1200 | 750 |

Example 5

Matrix fill compositions were prepared according to the composition shown in Table 8 and were encapsulated in a soft capsule shell. Matrix fills were physically and chemically stable after three months with no crosslinking of the soft capsule shell. Moisture analysis and pH measurements of the matrix fill before and after encapsulation were carried out under ICH stability conditions (25° C., 60% RH; 30° C., 65% RH; 40° C., 75% RH) for 0, 2, 3, or 6 months as shown in Table 9.

TABLE 9

Matrix Fill Moisture and pH Parameters

| Matrix Fill (180 mg Fexofenadine) | pH | Moisture (%) |
|---|---|---|
| Fill before encapsulation | 3.8 | 2.1 |
| Fill removed after drying (0 months) | 4.3 | 6.9 |
| Fill removed after storage at 40° C., 75% RH (1 month) | 4.9 | 6.6 |
| Fill removed after storage at 40° C., 75% RH (2 months) | 5.2 | 6.6 |
| Fill removed after storage at 40° C., 75% RH (3 months) | 5.3 | 6.7 |
| Fill removed after storage at 25° C., 60% RH (3 months) | 4.6 | 6.6 |
| Fill removed after storage at 25° C., 60% RH (3 months) | 4.9 | N/A |

TABLE 9-continued

Matrix Fill Moisture and pH Parameters

| Matrix Fill (180 mg Fexofenadine) | pH | Moisture (%) |
|---|---|---|
| Fill removed after storage at 30° C., 65% RH (6 months) | 5.2 | N/A |

Example 6

Matrix fill compositions were prepared according to the composition shown in Table 8 and were encapsulated in a soft capsule. Matrix fills were physically and chemically stable after three months with no crosslinking of the soft capsule shell. Optical microscopy observation studies were carried out after the capsules had been stored for 0, 3, and 6 months at 25° C., 60% RH and for 6 months at 20° C., 65% RH as shown in Table 10. The soft gelatin dosage form was determined to have passed the observation tests.

TABLE 10

Matrix Fill Physical Evaluation

| Matrix Fill (180 mg Fexofenadine) | Soft Capsule Appearance | Fill Appearance | Capsule Hardness (N = 5) | Result |
|---|---|---|---|---|
| After encapsulation and drying (0 months) | Oblong, clear, not sticky, and no discolouration of the capsules | Clear, no leaking and no precipitation of API | 8.1N | PASS |
| Storage at 25° C., 60% RH (3 months) | Oblong, clear, not sticky, and no discolouration of the capsules | Clear, no leaking and no precipitation of API | 6.2N | PASS |
| Storage at 25° C., 60% RH (6 months) | Oblong, clear, not sticky, and no discolouration of the capsules | Clear, no leaking and no precipitation of API | 6.4N | PASS |
| Storage at 20° C., 65% RH (6 months) | Oblong, clear, not sticky, and no discolouration of the capsules | Clear, no leaking and no precipitation of API | 4.6N | PASS |

Example 7

Matrix fill compositions were prepared according to the composition shown in Table 8 and were encapsulated in a soft capsule. Matrix fills were physically and chemically stable after three months with no crosslinking of the soft capsule shell. Degradation studies were carried out after storage of the soft capsules encapsulating the matrix fill described herein under ICH stability conditions (25° C., 60% RH; 30° C., 65% RH; 40° C., 75% RH) as shown in Table 11. The soft gelatin dosage form was determined to be stable with essentially no impurities.

TABLE 11

Matrix Fill Assay and Degradation Results

| Matrix Fill (180 mg Fexofenadine) | Fexofenadine (%) | % Related Compound | Unknown impurity | Results |
|---|---|---|---|---|
| After encapsulation and drying (0 months) | 101.2 | 0.1 | 0.1 | Pass |
| Storage at 40° C., 75% RH (1 month) | 101.3 | 0.2 | NA | Pass |
| Storage at 40° C., 75% RH (2 months) | 99.3 | 0.2 | NA | Pass |

TABLE 11-continued

Matrix Fill Assay and Degradation Results

| Matrix Fill (180 mg Fexofenadine) | Fexofenadine (%) | % Related Compound | Unknown impurity | Results |
|---|---|---|---|---|
| Storage at 40° C., 75% RH (3 months) | 98.9 | 0.2 | 0.1 | Pass |
| Storage at 25° C., 60% RH (3 months) | 99 | 0.1 | 0.1 | Pass |
| Storage at 30° C., 65% RH (6 months) | 98.2 | 0.2 | 0.1 | Pass |

Example 8

Matrix fill compositions were prepared according to the composition shown in Table 8 and were encapsulated in a soft capsule. Matrix fills were physically and chemically stable after three months with no crosslinking of the soft capsule shell. Dissolution studies of the soft capsules encapsulating the matrix fill described herein were carried out under USP test 3 conditions (0.001 N HCl) for 45 minutes after storage under ICH stability conditions (25° C., 60% RH; 30° C., 65% RH; 40° C., 75% RH) as shown in Table 12. Assessment of active release (fexofenadine) was determined by HPLC analysis. The percentage of fexofenadine release met or exceeded the percentage of release by a commercially available tablet form of fexofenadine.

TABLE 12

Matrix Fill Assay and Dissolution Results

| Matrix Fill (180 mg Fexofenadine) | Release (%) after 45 min | Results |
|---|---|---|
| After encapsulation and drying (0 months) | 95.3 | Pass |
| Storage at 40° C., 75% RH (1 month) | 95.4 | Pass |
| Storage at 40° C., 75% RH (2 months) | 94.3 | Pass |
| Storage at 40° C., 75% RH (3 months) | 88.9 | Pass |
| Storage at 25° C., 60% RH (3 months) | 96 | Pass |
| Storage at 30° C., 65% RH (6 months) | 97.1 | Pass |
| Commercial product | 91.6 | Pass |

What is claimed is:

1. An oral pharmaceutical composition comprising a matrix fill comprising:
   at least one solubility enhancing agent;
   at least one viscosity enhancing agent;
   at least one surfactant;
   at least one pH modifying agent;
   water; and
   at least one active pharmaceutical ingredient dissolved in the matrix fill;
   wherein the matrix fill comprises a single phase liquid that is encapsulated in a soft capsule shell.

2. The composition of claim 1, wherein the solubility enhancing agent comprises about 40% to about 85% of the matrix fill mass.

3. The composition of claim 1, wherein the viscosity enhancing agent comprises povidone, hydroxypropylmethylcellulose, hydroxypropylcellulose, gelatin, methylcellulose, acacia, xanthan gum, or tragacanth comprising from about 1% to about 10% of the matrix fill mass.

4. The composition of claim 1, wherein the surfactant comprises an anionic surfactant comprising sodium lauryl sulfate, sodium docusate, sodium stearate, or ammonium lauryl sulfate comprising from about 1% to about 7% of the matrix fill mass.

5. The composition of claim 1, wherein water comprises about 1% to about 7% of the matrix fill mass.

6. The composition of claim 1, wherein the pH-modifying agent comprises a carboxylic acid comprising tartaric acid, lactic acid, glutamic acid, aspartic acid, malic acid, succinic acid, or fumaric acid comprising from about 1% to about 3% of the matrix fill mass.

7. The composition of claim 1, wherein the matrix fill comprises an active pharmaceutical ingredient comprising about 5% to about 33% of the matrix fill mass; wherein the ratio of the active pharmaceutical ingredient to the total mass of the matrix fill is about 1:20 to about 1:3.

8. The composition of claim 2, wherein the solubility enhancing agent comprises polyethylene glycol, propylene glycol, or glycerol; or the solubility enhancing agent comprises polyethylene glycol and propylene glycol.

9. The composition of claim 7, wherein the matrix fill comprises an active pharmaceutical ingredient that is poorly soluble in water comprising acetaminophen, acetazolamide, acyclovir, allopurinol, amoxicillin, cefdinir, cefixime, cefotiam hexetil hydrochloride, cefpodoxime proxetil, cefuroxime axetil, dapsone, dexamethasone, doxycycline, famotidine, fexofenadine, folic acid, furosemide, glipizide, griseofulvin, hydrochlorothiazide, l-carbocysteine, levodopa, levosulpiride, linezolid, meloxicam, mesalamine, metoclopramide, modafinil, nabumetone, nalidixic acid, oxcarbazepine, oxycodone, phenobarbital, propylthiouracil, sulfadiazine, sulfamethoxazole, sultamicillin, theophylline, tosufloxacin, triflusal, trimethoprim, and zaltoprofen or pharmaceutically acceptable salts, isomers, prodrugs (e.g., esters) and derivatives thereof, and mixtures of any of the active pharmaceutical ingredients listed thereof.

10. The composition of claim 9, wherein the active pharmaceutical ingredient comprises fexofenadine.

11. The composition of claim 1, wherein the matrix fill comprises polyethylene glycol, propylene glycol, povidone, sodium lauryl sulfate, citric acid, water, and fexofenadine.

12. The composition of claim 11, wherein the matrix fill comprises:
   about 45% to about 65% polyethylene glycol;
   about 10% to about 20% propylene glycol;
   about 1% to about 5 povidone K90;
   about 2% to about 6% sodium lauryl sulfate;
   about 1% to about 3% citric acid;
   about 1% to about 3% water; and
   about 5% to about 20% fexofenadine hydrochloride.

13. The composition of claim 1, wherein the matrix fill is clear or transparent and is stable for at least about 6 months at 25° C. and 60% relative humidity.

14. A method for manufacturing a single phase liquid matrix fill composition comprising at least one solubility enhancing agent; at least one viscosity enhancing agent; at least one surfactant; at least one pH modifying agent; water; and at least one active pharmaceutical ingredient suitable for encapsulation in a soft capsule shell; wherein preparing the matrix fill comprises the steps of:
   (a) wetting and mixing the surfactant in water;
   (b) adding the one or more solubility enhancing agents and the one or more pH modifying agents and stirring the mixture;
   (c) dissolving the active pharmaceutical ingredient by stirring the mixture;
   (d) adding the viscosity enhancing agent and stirring the mixture; and
   (e) filtering the mixture through a filter cloth; and
   (f) degassing the matrix fill mixture.

15. The method of claim 14, wherein the matrix fill composition comprises polyethylene glycol, propylene glycol, povidone, sodium lauryl sulfate, citric acid, water, and fexofenadine.

16. The method of claim 14, wherein the prepared matrix fill is clear or transparent and is stable for at least about 6 months at 25° C. and 60% relative humidity.

17. The method of claim 14, wherein the prepared matrix fill has a pH of about pH 3.5 to about pH 7.5.

18. A method for manufacturing an oral pharmaceutical composition comprising a soft capsule shell or an enteric soft capsule shell and matrix fill comprising the steps of:
   (a) providing a matrix fill prepared by the method of claim 14;
   (b) providing a soft capsule gel mass or an enteric soft capsule gel mass;
   (c) casting the soft capsule gel mass into films using heat-controlled drums or surfaces; and
   (d) forming a soft capsule comprising the matrix fill composition using rotary die encapsulation technology.

19. A method for treating, reducing the symptoms or onset of, or prophylaxis of stemming from seasonal allergic rhinitis or chronic idiopathic urticaria with the composition of claim 1; wherein the active pharmaceutical ingredient comprises an anti-allergenic comprising fexofenadine.

20. A kit for dispensing the oral pharmaceutical composition of claim 1, comprising:
   (a) at least one soft capsule comprising a matrix fill comprising an active pharmaceutical ingredient;
   (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and
   (c) optionally, an insert comprising instructions or prescribing information for the active pharmaceutical ingredient.

* * * * *